(12) United States Patent
Christen et al.

(10) Patent No.: US 9,150,916 B2
(45) Date of Patent: Oct. 6, 2015

(54) COMPOSITIONS AND METHODS FOR IDENTIFYING THE ESSENTIAL GENOME OF AN ORGANISM

(76) Inventors: Beat Christen, San Francisco, CA (US); Mike Fero, San Francisco, CA (US); Eduaro Abeliuk, San Francisco, CA (US)

( * ) Notice: Subject to any disclaimer, the term of this patent is extended or adjusted under 35 U.S.C. 154(b) by 0 days.

(21) Appl. No.: 13/532,674

(22) Filed: Jun. 25, 2012

(65) Prior Publication Data

US 2013/0143745 A1     Jun. 6, 2013

Related U.S. Application Data

(60) Provisional application No. 61/501,073, filed on Jun. 24, 2011.

(51) Int. Cl.

| | |
|---|---|
| *C12N 15/74* | (2006.01) |
| *C12Q 1/68* | (2006.01) |
| *G06F 19/22* | (2011.01) |
| *C12N 15/10* | (2006.01) |
| *C12N 15/00* | (2006.01) |
| *C12Q 1/02* | (2006.01) |
| *C07H 21/04* | (2006.01) |

(52) U.S. Cl.
CPC .......... *C12Q 1/6874* (2013.01); *C12N 15/1065* (2013.01); *G06F 19/22* (2013.01)

(58) Field of Classification Search
None
See application file for complete search history.

(56) References Cited

U.S. PATENT DOCUMENTS

| | | | | |
|---|---|---|---|---|
| 6,207,384 | B1 * | 3/2001 | Mekalanos et al. | 435/6.18 |
| 2006/0014169 | A1 * | 1/2006 | Fiandt et al. | 435/6 |
| 2006/0234233 | A1 * | 10/2006 | Bruce et al. | 435/6 |
| 2009/0088327 | A1 * | 4/2009 | Rigatti et al. | 506/4 |

OTHER PUBLICATIONS

Gawronski et al., "Tracking insertion mutants within libraries by deep sequencing and a genome-wide screen for *Haemolphilus* genes required in the lung" 106(38) Proceedings of the National Academy of Sciences USA 16422-16427 (2009).*

Langridge et al., "Simultaneous assay of every *Salmonella* Typhi gene using one million transposon mutants" 19 Genome Research 2308-2316 (2009).*

Junker et al., "Global analysis of candidate genes important for fitness in a competitive biofilm using DNA-array-based transposon mapping" 152 Microbiology 2233-2245 (2006).*

Bateman et al., "Evaluation of a Tetracyline-Inducible Promoter in *Staphylococcus aureus* In Vitro and In Vivo and Its Application in Demonstrating the Role of sigB in Microcolony Formation" 69(12) Infection and Immunity 7851-7857 (2001).*

Radha et al., "Sustained expression of keratinase gene under PxylA and PamyL promoters in the recombinant *Bacillus megaterium* MS941" 99 Bioresource Technology 5528-5537 (2008).*

Scholle et al., "Whole-Genome Detection of Conditionally Essential and Dispenable Genes in *Escherichia coli* via Genetic Footprinting" 416 Methods in Molecular Biology 83-102 (2007).* van Opijnen et al., "Tn-seq: high-throughput parallel sequencing for fitness and genetic interaction studies in microorganisms" 6(10) Nature Methods 767-772 (including Supplemental Information) (2009).*

Phadnis et al., "Identification of base pairs in the outside end of insertion seqeunce IS50 that are needed for IS50 and TN5 transposition" 84 Proceedings of the National Academy of Sciences USA 9118-9122 (1987).*

* cited by examiner

*Primary Examiner* — Celine Qian
*Assistant Examiner* — Nancy J Leith
(74) *Attorney, Agent, or Firm* — Novak Druce Connolly Bove + Quigg LLP

(57) ABSTRACT

Compositions and methods are provided for the rapid and highly accurate identification of the entire essential genome of any organism under a given selection condition at a resolution of a few base pairs. An engineered transposon bearing an adapter sequence for ultra high throughput adaptor-based sequencing is employed for hyper-saturated transposon mutagenesis. Transposon junctions are subsequently isolated and collectively amplified through a shared parallel PCR strategy such that a second adaptor sequence is further incorporated into template DNA so that the first adaptor sequence and the second adaptor sequence flank the 5' and 3' regions of the sample DNA, respectively. Sample DNA is then sequenced in an ultra high-throughput adaptor-based DNA sequencer using adaptor primers. Transposon insertion sites are mapped onto the organism's genome, allowing for the algorithmic identification of essential genetic elements based on genomic transposition frequency.

18 Claims, 11 Drawing Sheets

SEQUENCE LISTING

```
<160> NUMBER OF SEQ ID NOS: 8

<210> SEQ ID NO 1
<211> LENGTH: 15
<212> TYPE: DNA
<213> ORGANISM: Artificial Sequence
<220> FEATURE:
<223> OTHER INFORMATION: O-end sequence of a transposon element

<400> SEQUENCE: 1
gtgtataaga gtcag                                                    15

<210> SEQ ID NO 2
<211> LENGTH: 53
<212> TYPE: DNA
<213> ORGANISM: Artificial Sequence
<220> FEATURE:
```

<223> OTHER INFORMATION: Primer

<400> SEQUENCE: 2
catatgggag atctgatcaa gagacaggtc gaccgatccc gtacacaagt agc    53

<210> SEQ ID NO 3
<211> LENGTH: 87
<212> TYPE: DNA
<213> ORGANISM: Artificial Sequence
<220> FEATURE:
<223> OTHER INFORMATION: Primer

<400> SEQUENCE: 3
agagctcgcg tcacactcat cggttgggtg acactctttc cctacacgac gctcttccga    60
tctacttgtg tataagagtc agttacc    87

<210> SEQ ID NO 4
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (34)..(43)
<223> OTHER INFORMATION: n is a, c, g, or t

<400> SEQUENCE: 4
ctcggcattc ctgctgaacc gctcttccga tctnnnnnnn nnnacgcc    48

<210> SEQ ID NO 5
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (34)..(43)
<223> OTHER INFORMATION: n is a, c, g, or t

<400> SEQUENCE: 5
ctcggcattc ctgctgaacc gctcttccga tctnnnnnnn nnncctgg    48

<210> SEQ ID NO 6
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (34)..(43)
<223> OTHER INFORMATION: n is a, c, g, or t

<400> SEQUENCE: 6
ctcggcattc ctgctgaacc gctcttccga tctnnnnnnn nnncctcg    48

<210> SEQ ID NO 7
<211> LENGTH: 58
<212> TYPE: DNA
<213> ORGANISM: Artificial Sequence
<220> FEATURE:
<223> OTHER INFORMATION: primer

<400> SEQUENCE: 7
aatgatacgg cgaccaccga gatctacact ctttccctac acgacgctct tccgatct    58

```
<210> SEQ ID NO 8
<211> LENGTH: 62
<212> TYPE: DNA
<213> ORGANISM: Artificial Sequence
<220> FEATURE:
<223> OTHER INFORMATION: primer

<400> SEQUENCE: 8
caagcagaag acggcatacg agatcggtct cggcattcct tgctgaaccg ctcttccgat      60
ct                                                                    62
```

COMPOSITIONS AND METHODS FOR IDENTIFYING THE ESSENTIAL GENOME OF AN ORGANISM

CROSS-REFERENCE TO RELATED APPLICATIONS

This application claims the benefit of Provisional Application Ser. No. 61/501,073 filed on Jun. 24, 2011, which is herein incorporated by reference in its entirety.

FIELD OF THE TECHNOLOGY

This technology relates generally to the field of synthetic biology, systems-genetics, molecular biology, and more specifically for identifying genetic features and decoding the essential genetic information of genomes.

SEQUENCE LISTING

The instant application contains a Sequence Listing which has been submitted in ASCII format via EFS-Web and is hereby incorporated by reference in its entirety. Said ASCII copy, created on Oct. 12, 2012 is named 13532673.txt and is 2,193 bytes in size.

BACKGROUND

The identification of the entire set of essential genetic instructions encoded in the bacterial genome is crucial for a complete understanding of the regulatory networks that run and program cells. The essential genome of any organism not only contains protein-coding sequences, but also essential structural elements, non-coding RNAs and regulatory sequences. The essential genome is not necessarily a static measure: it is dynamically associated with the environmental context in which an organism is placed. For instance, the essential genomic regions of an organism may differ depending upon the availability of certain foods or nutrients in the local environment. It may also depend on such factors as temperature or the presence of toxic compounds.

Traditional techniques have relied upon mutagenizing areas of the genome to abrogate the function of the adjacent genomic region, thus permitting the identification of locations that convey lethal phenotypes to an organism of interest. By mapping these lethality-inducing locations, a picture of an organism's essential genome emerges. Systematic techniques to attain such a map have been limited to the creation of in-frame deletion libraries in which each of the open reading frames (ORF) of a genome are shifted such as to render the corresponding translated region null. However, on a genome-wide level, such a method would require the laborious mutation and analysis of thousands of individual genes in a given organism. Moreover, such an approach fails to identify the essential, regulatory sequences, transcription factor binding sites, structural genome maintenance and replication features as well as non-coding regions of a genome.

In this respect, transposon mutagenesis has proven to be a valuable, high throughput tool to create mutagenic libraries. Catalyzed by transposase enzymes, transposable elements may be randomly incorporated into a host genome to create large insertional mutations. Due to their size, transposons functionally interfere with the respective transposed region, allowing for a forward genetic approach of identifying particular genes associated with a given phenotype. For essential genomic regions under a particular selective condition, such transposon insertions renders an organism unviable and are not recovered.

For genomic studies in bacteria, plasmids containing a transposable element and transposase can be individually transformed into bacteria and selectively cultured. Integration locations can then be identified through the amplification and sequencing of transposon junctions using specifically tailored primers and cross-referencing the data with the underlying bacterial genomic sequence. Regions corresponding to low levels of integration tolerance likely serve an essential function within the genome under a particular selective condition. However, this approach has been limited in significant aspects.

In light of the expansiveness of genomes, traditional low-throughput sequencing techniques to map transposon insertion sites present an unwieldy challenge: DNA from individual clones must be independently amplified, purified, and sequenced. Greater levels of resolution in discerning genomic regions of insertional tolerance will necessarily succumb to increasing cost and labor restraints. Moreover, low mapping throughput of existing methods permits only analysis of transposon libraries with low insertion complexity. This directly translates in a poor genomic resolution, which also proves problematic as transposase-mediated insertions demonstrate partial sequence bias, and thus insertion bias will distort the results of any analysis.

Ultra high-throughput sequencing strategies exist to enable a more saturated transposon mutagenesis strategy that could potentially overcome this bias issue. For example, the advent of primed synthesis in flow cells has allowed for massive parallel sequencing of millions of different short DNA templates. For instance, Illumina's sequencing by synthesis (SBS) technology can generate up to 55 gigabases (Gb) of sequencing data in a day. In this technology, adaptors complimentary to oligomers on a planar optically transparent flow cell surface are first ligated to the ends of template DNA. Subsequently, adapted single-stranded DNAs are bound to the flow cell and amplified by a process known as solid-phase "bridge" PCR. Specifically, in each PCR cycle, the loose end of a tethered DNA template arches and hybridizes to a tethered oligomer located in the vicinity on the flow cell surface. As PCR proceeds, DNA polymerase creates a double-stranded bridge between the two attached termini, resulting in two anchored single-stranded templates upon denaturation. Subsequent rounds thus generate clusters of clonally-amplified DNA of up to 1,000 identical copies, allowing for the direct visualization of fluorescently-labeled deoxytrinucleoside triphosphates (dNTPs). Such a technique results in densities on the order of ten million single-molecule clusters per square centimeter. Following cluster generation, four labeled reversible dNTP terminators, along with primers and DNA polymerase, are introduced into the flow cell for the first cycle of sequencing. Incorporated dNTPs, each bearing a different, discernable fluorophore, are then visualized through laser excitation and subsequently enzymatically cleaved and washed away for the next cycle. To this extent, the sequencing cycles are repeated to determine the sequence of bases in a DNA template, one base at a time.

One of the key innovations underlying this system and related ultra high-throughput adaptor-based sequencing strategies involves the use of adaptor sequences, which allows for in-situ template "bridge" amplification for cluster generation. Such clonal clustering, as noted previously, enables direct fluorescent visualization of high densities of DNA samples for sequencing purposes. However, this approach typically calls for the use of conventional DNA isolation, fragmentation, and ligation protocols—a laborious and time-consuming process that is necessary to ensure DNA of a suitably small size bear compatible adaptor ends for bridge amplification.

Moreover, attempts to utilize this ultra high-throughput sequencing strategy to overcome the insertion bias of low-density studies by pooling clones and sequencing transposon flanking regions en masse has ultimately resulted in short genomic reads on the order of approximately 16 bp. Given the repetitious nature of genomes, such small identified genomic sequences would prevent an accurate and robust identification of all transposon insertion sites and thus limit the dissection of the essential genome of an organism.

SUMMARY

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by the practice of the principles set forth herein.

In order to facilitate the rapid and scalable dissection of the essential genome of an organism, the presented technology combines the high genomic resolution provided by hyper-saturated transposon mutagenesis with ultra-high-throughput sequencing strategies. Such an approach allows for the rapid profiling of any genome for all essential genetic elements under a particular selection condition at a fraction of the time and cost of traditional methods.

The present technology provides for an engineered transposon, a PCR strategy, and an algorithm that facilitates rapid, direct analysis of an organism's essential genome in an ultra-high-throughput adaptor-based DNA sequencer, features of which obviate the need for several expensive and time consuming process steps used in these sequencing protocols.

In general, the technology features compositions and methods for rapidly identifying essential genetic elements under a particular selection condition by pooling and isolating transposon junctions using a shared PCR strategy while further integrating ultra high-throughput DNA sequencer adaptor ends into this template DNA. As this template DNA bears transposon junctions from hyper-saturated transposon mutagenic assays, this allows for direct high-throughput sequencing of junctions to identify genomic integration sites—in turn enabling identification of essential genetic elements through negative mapping. The method and compositions include: a) performing hyper-saturated transposon mutagenesis by delivering engineered transposon bearing a first adaptor sequence, b) isolating transposon junctions while integrating a second adaptor sequence in the template DNA using a shared, parallel PCR amplification strategy such that the template DNA ultimately bears the first adaptor sequence at its 5' end and the second adaptor sequence at its 3' end, c) running the sample in a ultra high-throughput DNA sequencer, and d) algorithmically locating the essential regions of the genome through detection of regions sufficiently absent in transposon insertions.

In some embodiments, a Tn5 transposable element is engineered with sequences allowing direct application to ultra high throughput DNA sequencing methods without the need for conventional DNA isolation, fragmentation, and ligation protocols. In some embodiments, the Tn5 transposable element is engineered to include a promoter at one end pointing outwards, such that, depending on the insertion orientation the Tn5 element will cause disruption of or will permit initiation of adjacent genetic elements. This Tn5 element includes a ribosomal binding site as well as a start codon located between the promoter element and the transposon end to allow translation initiation at the engineered start codon and cause translation of downstream sequences at the site of transposon insertion. In some embodiments, a second ribosomal binding site is also included, located after the engineered start codon. This second ribosomal binding site allows initiation of translation at a start codon at the native start codon or at a internal start site within downstream open reading frames at the site of transposon insertion.

A hyper-saturated transposon mutagenesis strategy is employed to provide high resolution of the critical parts of a genome under a given selection condition. Although a given individual cell bears a single transposon insertion event with the engineered transposable element, pooling of transformed cells allows for the identification of hundreds of thousands of insertion events. In some embodiments, over the span of an entire genome, this strategy allows detection of insertion event spaced less than 8 bp apart on average, allowing for the clear-cut demarcation of essential genomic regions. However, it will be appreciated that the actual average number of base pairs between each insertion event can vary.

This strategy is made possible by directly amplifying transposon junctions from pooled mutants using a semi-arbitrary nested PCR strategy. This approach uses a specific primer annealing from within the transposon end in conjunction with semi-arbitrary primers that anneal from outside it, generating an amplicon that bears the insertion interface and a relative large portion of genomic DNA. Specifically, semi-arbitrary primers each carry a different, random penta-nucleotide sequence, permitting on average an annealing to a genome of interest every 300 base-pairs while not permitting amplification of sequences corresponding to the transposon delivery plasmid. This in turn allows for specific amplification of all transposon junctions from large mutant pools simultaneously, insuring high coverage of the target genome by permitting amplification from multiple annealing points within the genome. Overall, this leads to greater sequencing lengths over the transposon junction in ultra high-throughput sequencers relative to previous techniques, discussed above, thus permitting a robust and accurate identification of insertion sites within a large genome.

In a preferred embodiment, an algorithm is employed for robust detection of genome regions with low transposon insertion frequencies and biases in transposon insertion orientation under a particular selection condition using an essential region heuristic, allowing high resolution identification of non-disruptable genomic regions including: essential protein coding, non-coding RNAs, essential regulatory elements such as promotor regions, 5' and 3' untranslated regions, as well as anti-sense transcripts and structural genome features. Specifically, from the sequencing string read outs, the algorithm identifies and maps genomic sequences by first identifying the O-end sequence from the inserted transposon element and then removing the sequence as well other non-native sequences. The location of the insertion is then ascertained and for insertions within coding regions, the insertion frame is also determined since this will effect whether the transposon element abrogates protein production or function. In some embodiments, the algorithm uses the average density of transposon insertions over the span of an ORF as well as the length of the longest internal non-disruptable sequence and the length of the non-disruptable 5' region of the ORF as a heuristic for determining essential ORFs. In some embodiments, the algorithm employs a similar frequency-based heuristic for identifying non-disruptable non-coding regions. In some embodiments, the algorithm detects bias in transposon insertion orientation. Specifically, the algorithm can identify essential promoter regions by calculating the distance between the annotated start codon of an essential ORF and the first anti-sense transposon insertion upstream: these anti-sense insertions are lethal within the essential promoter region as they abgrogate transcription of the essential ORF downstream. In some embodiments, the algorithm can identify cyto-toxic genetic elements by instances of insertional bias as transposition events that initiate adjacent cyto-toxic elements will be lethal, so these regions will be predisposed towards deactivating orientations.

Identification of essential genetic elements is vital to the understanding of genomes. The identification of essential genes has been a difficult, time intensive and costly process as gene essentiality depends on the particular niche of the organism. This method allows rapid and global identification of genetic features required for specific environments or conditions. The use of a negative mapping approach allows for the rapid screening for all essential elements at a fraction of the time and cost of traditional methods while the use of an engineered transposon obviates the need for several expensive and time consuming process steps used in high throughput sequencing protocols. Applications include 1) the identification of genes involved in pathogenicity and persistence in host organisms; 2) identification of genes involved in antibiotic resistance; 3) identification of pathways involved in specific metabolic or catabolic reaction networks such as those useful for biofuel production or bioremediation applications; and 4) identification of cyto-toxic genetic elements which may provide novel targets for anti-microbial drug development.

Unless otherwise defined, all technical terms used herein have the same meaning as commonly understood by one of ordinary skill in the art to which this technology belongs.

As used herein, a "nucleic acid" or a "nucleic acid molecule" means a chain of two or more nucleotides such as RNA (ribonucleic acid) and DNA (deoxyribonucleic acid).

As used herein, the term "protein" means any peptide-linked chain of amino acids, regardless of length or post-translational modification, e.g., glycosylation or phosphorylation.

By the term "bacteria" is meant a prokaryotic organism whose single cells have neither a membrane-enclosed nucleus and generally do not harbor membrane-bound organelles.

By the term "organism" is meant any prokaryotic or eukaryotic living system.

As used herein, the term "gene" is meant a nucleic acid molecule that codes for a particular protein, or in certain cases, a functional or structural RNA molecule.

As used herein, the term "open reading frame" or "ORF" is meant the portion of DNA that encodes a protein. The open reading frame begins with a translation start codon and ends with a stop codon.

By the term "non-coding DNA" is meant components of an organism's DNA sequence that does not encode for protein sequences. Such non-coding regions have significant roles, for instance, in regulating gene expression and creating functionally important non-coding RNAs.

As used herein, the term "essential genomic region" is meant a given stretch of DNA that is necessary for cell growth and/or viability under a given selection condition and thus tolerates little to no insertional mutations. Essential genomic regions may include, for example, protein-coding sequences, essential structural elements, non-coding RNAs and regulatory sequences.

As used herein, the phrase "under a particular selection condition" or "under a given selection condition" is meant the specific environment or condition in which an organism is selected. The essential genome of an organism is context specific and thus different selection conditions may yield different essential regions of the genome. For instance, different protein coding regions may be essential for a particular bacteria to be grown in media lacking specific nutrients, or more generally, to have viability in one host versus another.

As used herein, the phrase "hypersaturated transposon mutagenesis" means that transposon insertion events in a given bacterial sample will cumulatively cover at least every one hundred bps, and preferably every ten bps of the bacteria's genome, and more preferably at least eight bps of a bacteria's genome, thus providing a genomic resolution of at least eight bps for deducing essential genomic regions.

By the term "transposon" is meant a DNA molecule that is capable of integrating into a target DNA molecule, without sharing homology with the target DNA molecule. Transposon integration is catalyzed by transposase enzyme, which may be encoded by the transposon itself, or may be exogenously supplied. One example of a transposon is Tn5. Other examples include Mariner, Tn7, and Tn10.

By the term "transposon junction" is meant the interface between an inserted transposon and a native genomic sequence. Integration locations may be readily identified by employing a set of primers—one which binds on one end the transposon sequence and the other which binds the native genomic sequence on the other end such that the PCR amplified segment incorporates the junction. These junctions may then be sequenced across, and the corresponding genomic insertion sites may be identified by cross-referencing sequence data with the underlying bacterial genomic sequence.

By the phrase "ultra high-throughput adaptor-based DNA sequencing" is meant a sequencing technology that employs oligomer adaptors for generating clonal clusters of template DNA through solid-phase bridge amplification that is subject to gene sequencing. In one example of this technology, flow-cell sequencing technology employs a planar optically transparent flow cell surface harboring short adaptor oligomers linked to its surface complimentary to adaptor sequences on the ends of template DNA to be sequenced. Short single-stranded DNA (ssDNA) template (100-1000 bp) is bound to the flow cell surface and high densities of ssDNA clonal clusters on the order of ten million clonal clusters per square centimeter are generated through a process known as solid-phase bridge amplification. During this bridge PCR amplification, in which dNTPs and DNA polymerase are introduced to the flow cell, the loose end of a bound DNA template first arches and hybridizes to a linked adaptor oligomer located in the vicinity of the flow cell surface. DNA polymerase then creates a double-stranded bridge between the two attached termini, resulting in two anchored ssDNA templates upon denaturation. Through subsequent rounds, clusters of up to 1,000 identical copies of ssDNA template are created. For sequencing, four labeled reversible dNTP terminators, along with primers and DNA polymerase, are introduced into the flow cell. Incorporated dNTPs, each bearing a different, discernable fluorophore, are then visualized through laser excitation and subsequently enzymatically cleaved and washed away for the next cycle. Sequencing cycles are then repeated to determine the sequence of bases of DNA template, one base at a time. Larger sequences of DNA may also be sequenced by fragmenting the DNA, sequencing the fragments, and reconstructing them. A notable example of an ultra high-throughput adaptor-based DNA sequencer is the Illumina GAIIx instrument, although this technology is not limited only to such flow-cell based DNA sequencers.

By the term "adaptor end" is meant oligomers that are used for ultra high-throughput adaptor-based gene sequencing and which participate as primers for solid-phase bridge amplification as well as for sequencing. For example, in using an Illumina GAIIx flow-cell DNA sequencer, adaptors PE 1.0 and PE 2.0 may be used. For the purposes of this technology, DNA sequencer adaptor ends are also directly integrated into the 5' and 3' regions of template DNA through PCR to facilitate their application to an ultra high-throughput sequencer. This avoids the conventional and laborious approach of ligating adaptor ends to template DNA in sequencing protocols.

By the term "semi-arbitrary primer" is meant an oligomer that contains a defined 3' penta-nucleotide sequence, an interspacing 10 bp long arbitrary sequence that can be longer or shorter, and a 5' ultra high-throughput DNA sequencer-paired adaptor sequence. The defined 3' pentanucleotide sequence is designed so that it will anneal on average every 300 bp through the genome of interest, but does not permit amplification of sequences corresponding to the transposon delivery plasmid. Multiple semi-arbitrary primers may be employed to insure high coverage of the target genome by permitting amplification from multiple annealing points within the genome. The 5' adaptor sequence may, for example, be the Illumina-paired adaptor sequence PE 2.0, which can be used with the Illumina GAIIx flow cell DNA sequencer. However, the 5' adaptor may be an adaptor suitable to any other ultra high-throughput adaptor-based sequencer.

By the term "negative mapping" is meant deducing the essential genomic regions of a bacteria by identifying genomic regions that have little to no transposition insertions following transposon mutagenesis. Insertions of large transposon elements within these regions would abrogate their respective essential functions, thus rendering the bacteria unviable.

By the term "cyto-toxic genetic element" is meant a genetic element whose upregulation will result in a lethal phenotype for an organism. Orientation bias of inserted transposons in the antisense direction bearing an outwards facing promoter is used to identify cyto-toxic elements as sense insertions preceding these elements will cause upregulation of these elements, thus rendering a bacterium unviable.

By "selectable marker" is meant a gene carried by a transposon that alters the ability of a cell harboring the transposon to grow or survive in a given growth environment relative to a similar cell lacking the selectable marker. Such a marker may be a positive or negative selectable marker. For example, a positive selectable marker (e.g. an antibiotic resistance or auxotrophic gene) encodes a product that confers growth or survival abilities in selective medium (e.g., containing an antibiotic or lacking an essential nutrient). A negative selectable marker, in contrast, prevents transposon-bearing cells from growing in negative selection medium, when compared to cells not bearing the transposon. A selectable marker may confer both positive and negative selectability, depending upon the medium used to grow the cell. The use of selectable markers in prokaryotic cells is well known by those with skill in the art.

By the term "essential promoter region" is meant the minimum upstream genomic region of an essential protein or RNA coding region necessary for cell viability. In identifying these regions using hyper-saturated transposon mutagenesis that employs a transposable element bearing an outward facing promoter, insertions within the promoter region of an essential gene are only viable if the transposon-specific promoter is oriented in the sense direction; insertions in the anti-sense direction are lethal. Thus, the distance between the annotated start codon of the open reading frame of an essential gene and the first detected occurrence of an anti-sense insertion with the upstream region defines its essential promoter region.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof, which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings in which.

DETAILED DESCRIPTION

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure.

Described are compositions and methods for performing an ultra high-throughput screen of the essential genome of an organism using an engineered transposon that facilitates rapid genomic analysis by integrating DNA sequencer adaptor ends into template DNA.

Figure 1:
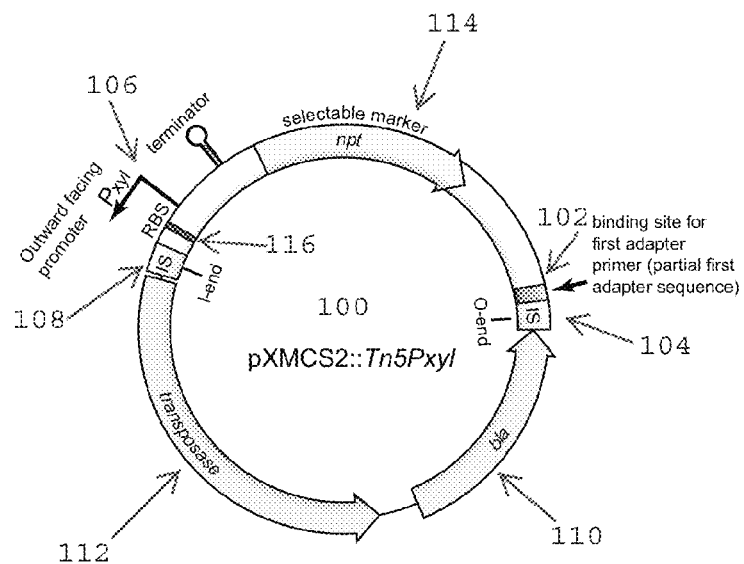
FIG. 1 illustrates an exemplary embodiment of the engineered transposable element.
Figure 9:
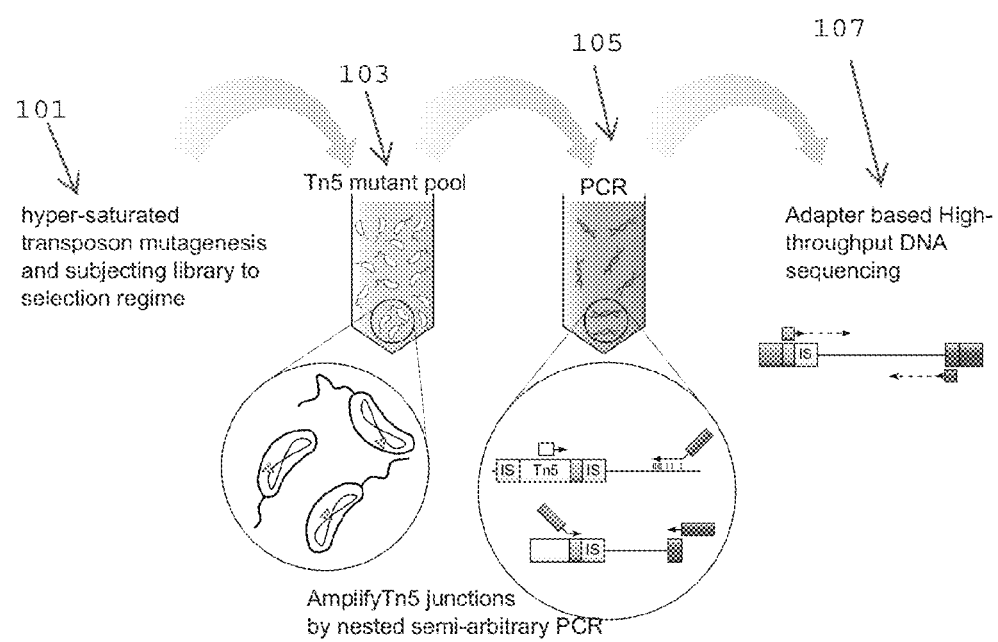
FIG. 9 is an illustration outlining a method for performing hyper-saturated mutagenesis for identifying the essential genome of an organism.

The first step of the process involves engineering a transposon delivery plasmid 100 to be delivered into an organism of interest such as plasmid 100 (FIGS. 1, 9). In some embodiments, traditional molecular cloning techniques were employed to construct a plasmid 100 which bears an Illumina paired-end adapter sequence 102 (PE 1.0, Illumina, Hayward, Calif.) adjacent to a Tn5 O-end insertion sequence (IS) element 104 as well as an outwards facing promoter adjacent 106 to the Tn5 I-end insertion sequence element 108 such that, depending on insertion orientation, the Tn5 element will cause disruption of or will permit initiation of adjacent genetic elements. These IS elements 104, 108 in turn flank an ampicillin resistance gene 110 and the Tn5 transposase 112, respectively (FIG. 1). Within the Tn5 transposable element, an antibiotic resistance cassette 114 is included to allow for selection of transformed cells that are transposed (FIG. 1). Moreover, the Tn5 element also includes a ribosomal binding 116 site as well as a start codon located between the promoter element 106 and the transposon end 108 (FIG. 1). This allows translation initiation at the engineered start codon and causes translation of downstream sequences at the site of transposon insertion. In some embodiments, there is a second ribosomal binding site located after the engineered codon. This second ribosomal binding site allows initiation of translation at a start codon at the native start codon or at a cryptic internal start site within the downstream open reading frames at the site of transposon insertion. In some embodiments, the engineered transposon delivery plasmid may include adaptor sequences 102 tailored for other ultra high-throughout adaptor-based DNA sequencers as well as the use of other transposon systems. Additionally, other selectable markers 114 may be employed within the engineered transposon delivery plasmid as well as in the transposon element. In various embodiments, different outward facing promoters 106 may be used, for example a Pxyl promoter.

The second step of the process involves identifying 101 viable transposition events under a particular selection condition (FIG. 9). In some embodiments, bacteria are selected on plates at 37° C. containing factors that correspond to the selectable marker 114 on the Tn5 transposable element (FIG. 1). For instance, a neomycin phosphotransferase (npt) gene may be incorporated in the transposable element, which would confer resistance to aminoglycoside antibiotics such as kanamycin, neomycin, or paromomycin upon transposition. However, other embodiments may impose different selection conditions, differing by such variables as temperature and nutrient levels.

After colonies have formed, they are then pooled 103 and subsequently subjected 105 to the same parallel PCR amplification strategy for DNA fragments covering transposon junctions (FIG. 9). This strategy importantly enables a hypersaturated transposon mutagenic approach for essential genomic analysis, which provides high resolution of the critical parts of a genome under a given selection condition. Although a given transformed cell bears at most one transposon insertion event with the engineered transposable element, pooling of transformed cells allows for the identification of hundreds of thousands of insertion events. Over the span of an entire genome, this would represent an insertion event approximately every 10 bp on average, allowing for the clear cut demarcation of essential genomic regions. However, the specific average number of base pairs between insertion events can vary and be greater or less than 10 bps, but the actual average number of base pairs between insertion events should be small enough that sufficient resolution of the genome is achieved so as to accurately identify essential genomic regions.

Figure 2A:
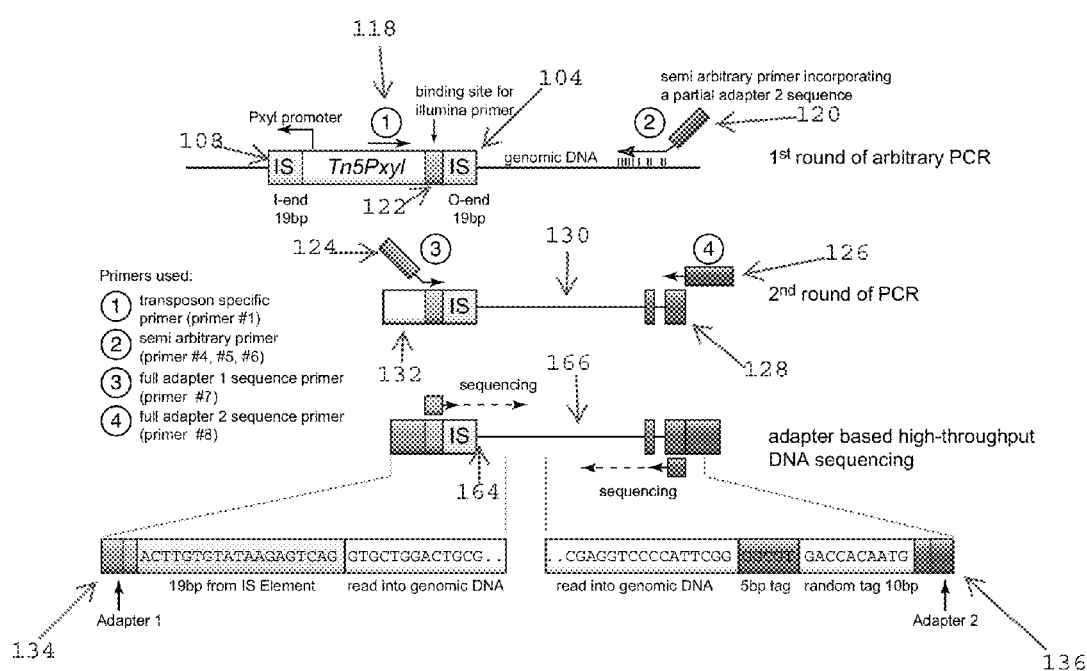
FIG. 2A illustrates an exemplary nested, parallel PCR amplification strategy.
Figure 2B:
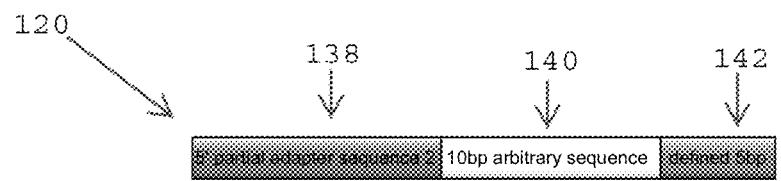

As part of this unique pooling process, cell cultures representing hundreds of thousands of different transposon insertion mutants may directly be added to each PCR reactions as template, along with two distinct sets of primers 118, 120. In some embodiments, the first primer 118 represents a transposon-specific primer that points outwards of the Tn5 element while the second primer 120 represents a set of semi-arbitrary primers designed to permit specific amplification of all transposon junctions from large mutant pools simultaneously (FIG. 2A). To this extent, one primer 118 anneals from within the transposon end in conjunction with semi-arbitrary primers 120 that anneal from outside it, generating a tremendous diversity of amplicons that bear the insertion interface 164 and a relative large portion of genomic DNA 130. These sequence strings in turn will allow for the accurate and robust mapping of insertion events onto a genome of interest in relatively few molecular biological steps. In some embodiments, each semi-arbitrary primer 120 contains a defined 3' penta-nucleotide sequence 142, an interspacing 10 bp long arbitrary sequence 140, and a 5' Illumina-paired adaptor sequence 138 (PE 2.0, Illumina, Hayward, Calif.) (FIG. 2B). The semi-arbitrary primers 120 possess different 3' penta-nucleotide sequences 142 that anneal on average every 300 bp throughout the genome of interest, but do not permit amplification of sequences corresponding to the transposon delivery plasmid. This permits specific amplification of all transposon junctions from large mutant pools simultaneously. The use of multiple penta-nucleotide sequences 142 insures high coverage of the target genome by permitting amplification from multiple annealing points within the genome. In some embodiments, the semi-arbitrary primer 120 may contain a 5' adaptor sequence 138 compatible with other ultra high-throughput adaptor-based DNA sequencers.

After a first round of PCR, PCR products are further amplified 105 in a second nested PCR step using two further, distinct primers 124, 126 (FIGS. 2A, 9). In some embodiments, the first primer 124 anneals to the engineered Illumina paired-end sequence adjacent to the transposon O-end 108 (FIG. 2A). The second primer 126 anneals to the 5' tag sequence 138 previously introduced by the first-round semi-arbitrary primers 120 (FIG. 2A). Overall, this nested PCR process results in template DNA 166 composed of a transposon genomic junction 164 flanked by Illumina adaptor ends 134, 136, allowing for direct application to an Illumina flow cell DNA sequencer following size exclusion and purification by agarose gel electrophoresis (FIG. 2A). Some embodiments may employ primers 124, 126 that anneal to adaptor sequences compatible with other ultra high-throughput adaptor-based DNA sequencers and which further generate amplicons 166 flanked by adaptor ends 134, 136 for direct application to such DNA sequencers.

Figure 3:
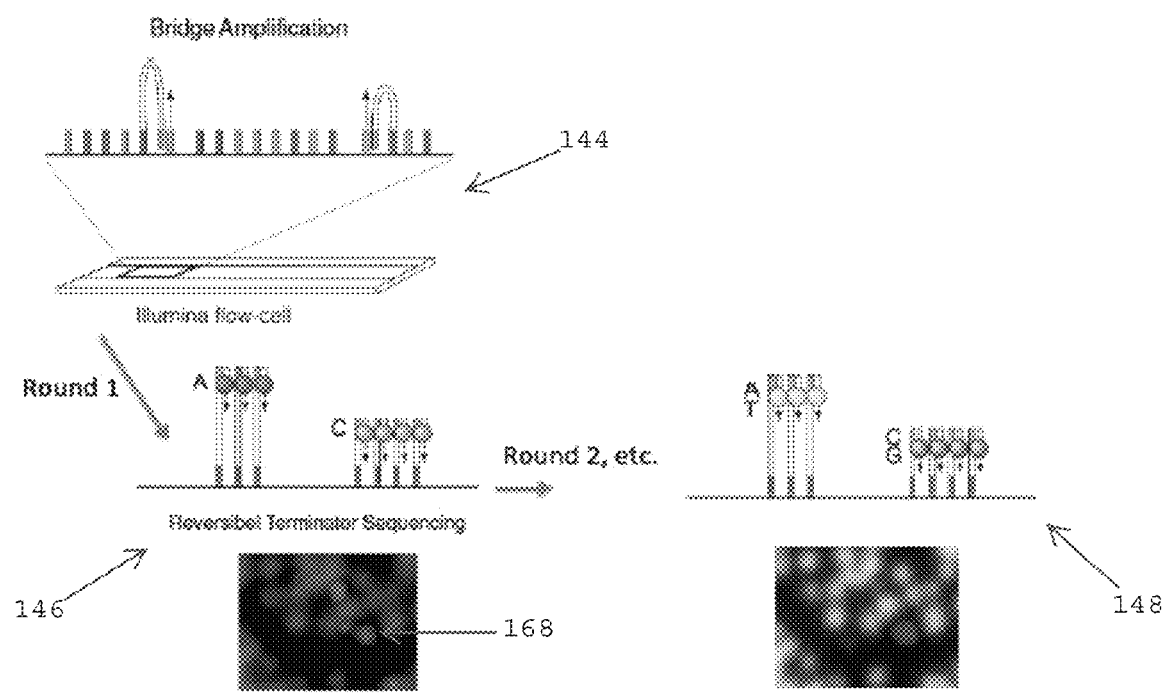
FIG. 3 illustrates an exemplary application of template DNA bearing flanking adaptor sequences to a adaptor-based DNA sequencer.

The third step of the process involves sequencing 107 the isolated transposon junctions using ultra high-throughput adaptor-based gene sequencing technology (FIG. 9). In some embodiments, an Illumina-based flow cell DNA sequencer is used. Briefly, adapted single-stranded template DNA is bound to the planar optically transparent flow cell surface and amplified by a process known as solid-phase "bridge" PCR 144 (FIG. 3). Specifically, in each PCR cycle, the loose end of the tethered DNA template arches and hybridizes to a tethered adaptor located in the vicinity on the flow cell surface. As PCR proceeds, DNA polymerase creates a double-stranded bridge between the two attached termini, resulting in two anchored single-stranded templates upon denaturation. Subsequent rounds thus generate clusters of clonally-amplified DNA 168 of up to 1,000 identical copies, allowing for the direct visualization of fluorescently-labeled deoxytrinucleoside triphosphates (dNTPs). Such a technique results in densities on the order of ten million single-molecule clusters per square centimeter. Following cluster generation, four labeled reversible dNTP terminators, along with primers and DNA polymerase, are introduced into the flow cell for the first cycle of sequencing 146. Incorporated dNTPs, each bearing a different, discernable fluorophore, are then visualized through laser excitation 168 and subsequently enzymatically cleaved and washed away for the next cycle (FIG. 3). To this extent, the sequencing cycles are repeated to determine the sequence of bases in a DNA template, one base at a time. In some embodiments, other ultra high-throughput adaptor-based DNA sequencers may be employed to generate sequencing data.

Figure 4:
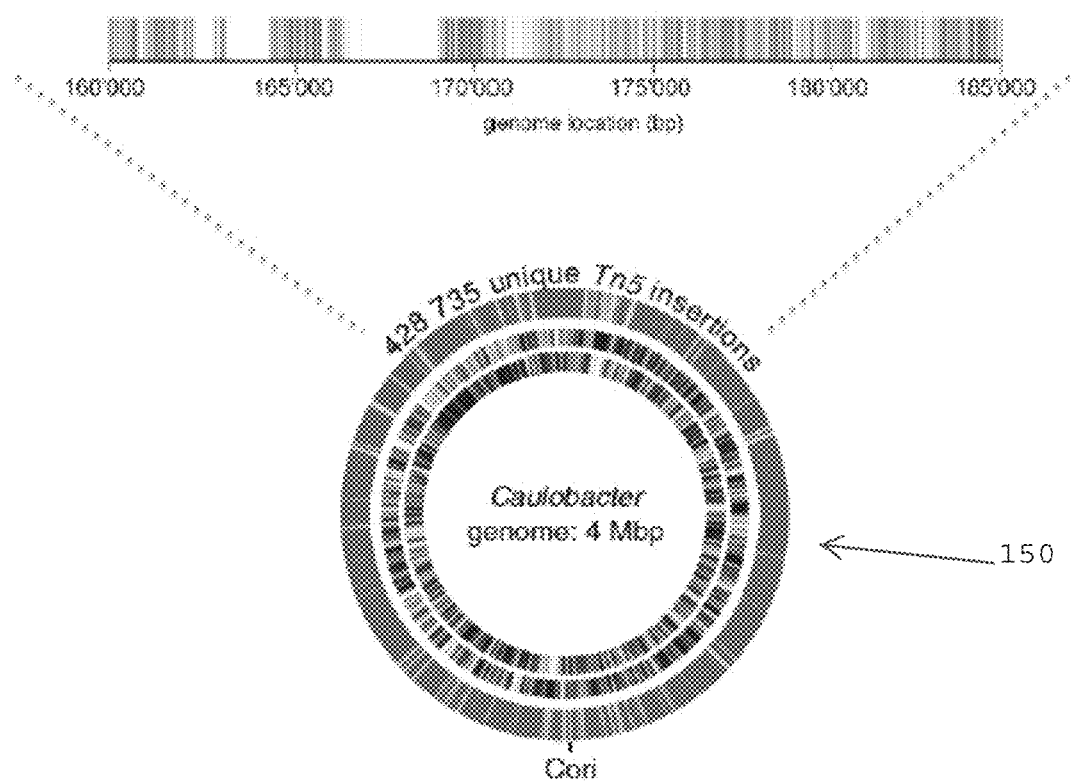
FIG. 4 illustrates an example of mapping transposition sites in the *Caulobacter crescentus* genome after hyper-saturated transposon mutagenesis.

Base-calling from raw fluorescent images may be performed using the genome analyzer software suite OLB version 1.6 (Illumina), or similar software suited to other ultra high-throughput adaptor-based DNA sequencers. The resulting sequence data is then used by an algorithm to identify 184 and map transposon insertion sights by extracting the relevant genomic sequence from the transposon junction sequence data and cross-referencing it with the bacterial genome of interest 150 (FIGS. 4, 9, 10).

Figure 5:
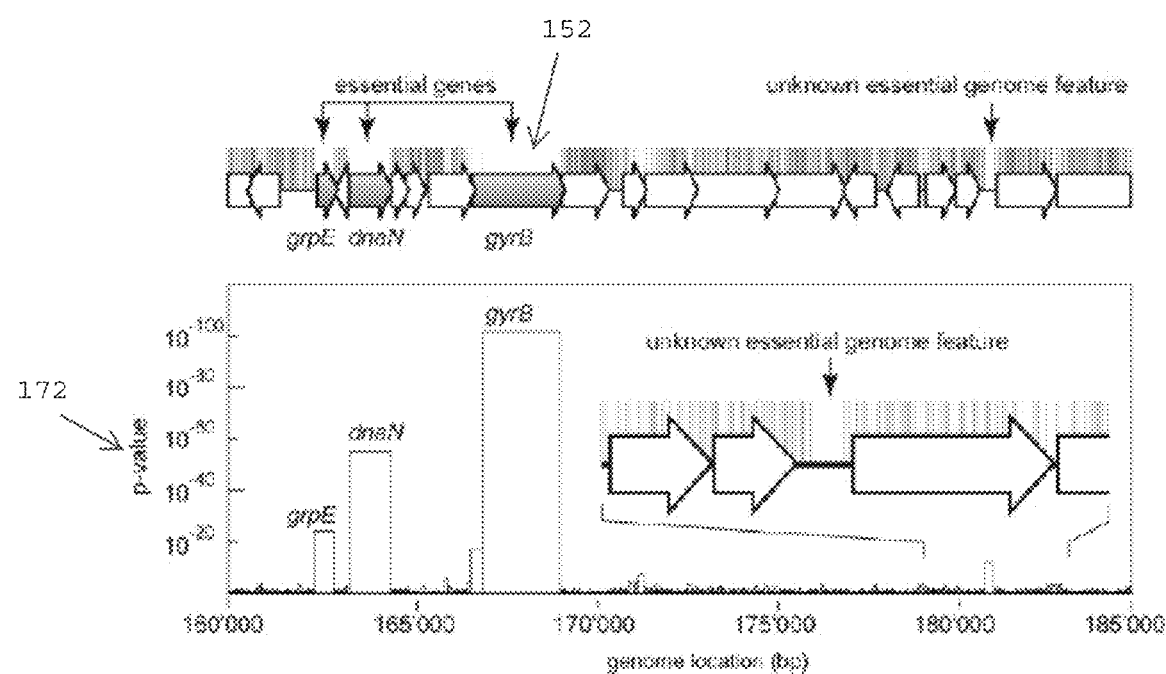
FIG. 5 illustrates an exemplary map of transposon insertions allowing for identification of known and unknown essential genome features in *Caulobacter crescentus*.
Figure 6A:
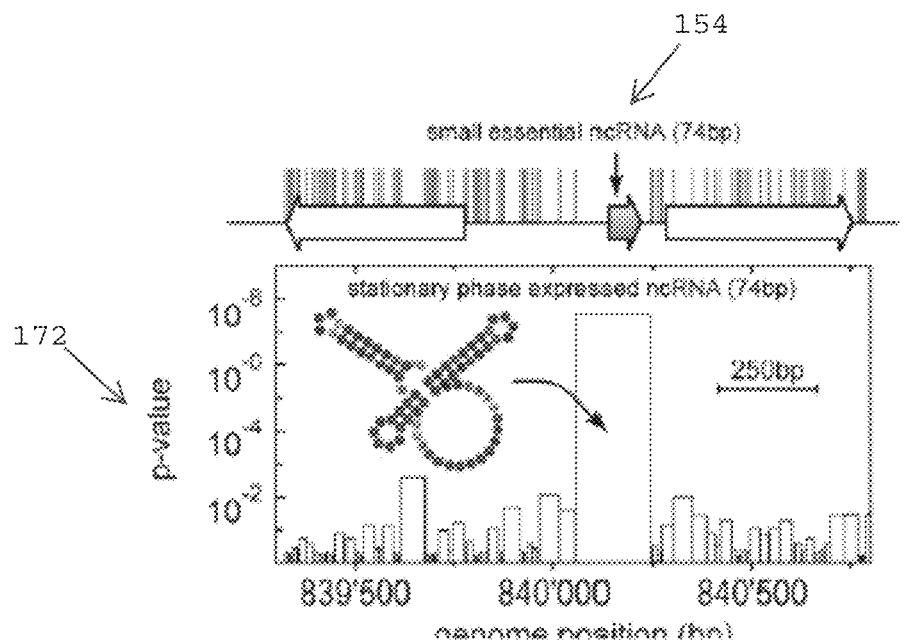
FIGS. 6A and 6B illustrates an example of identifying a small essential noncoding RNA and an essential protein domain in *Caulobacter crescentus*, respectively.
Figure 6B:
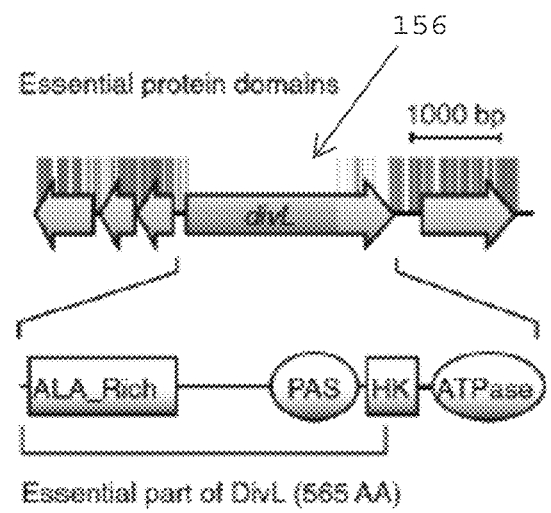
Figure 7:
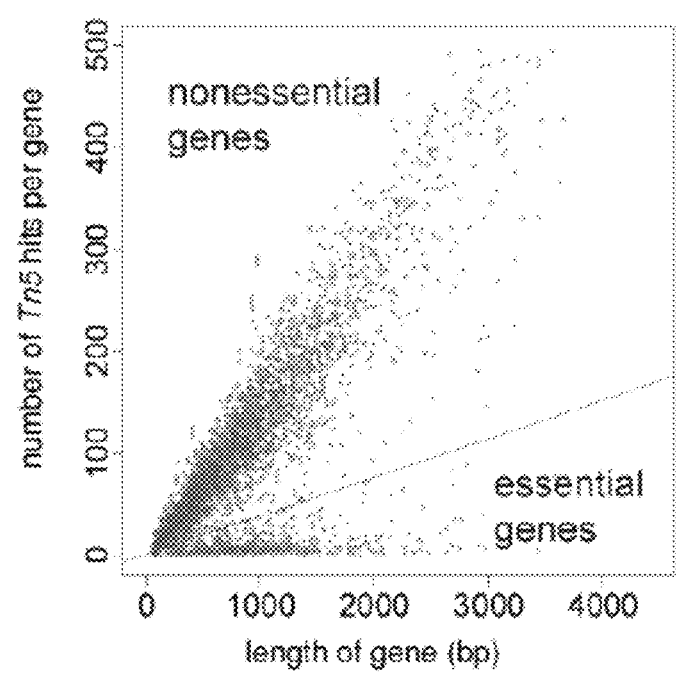
FIG. 7 illustrates an example of a scatter plot mapping of Tn5 insertion frequencies among essential and nonessential genes in *Caulobacter crescentus* showing a marked reduction in transposon insertions in essential genes.

An algorithm can then determine, based on genomic insertion frequency and bias, the identity of essential protein-coding sequences 152, protein domains 156, non-coding sequences, structural elements, non-coding RNAs 154, cytotoxic element, and regulatory sequences 162 (FIGS. 5-7).

Figure 10:
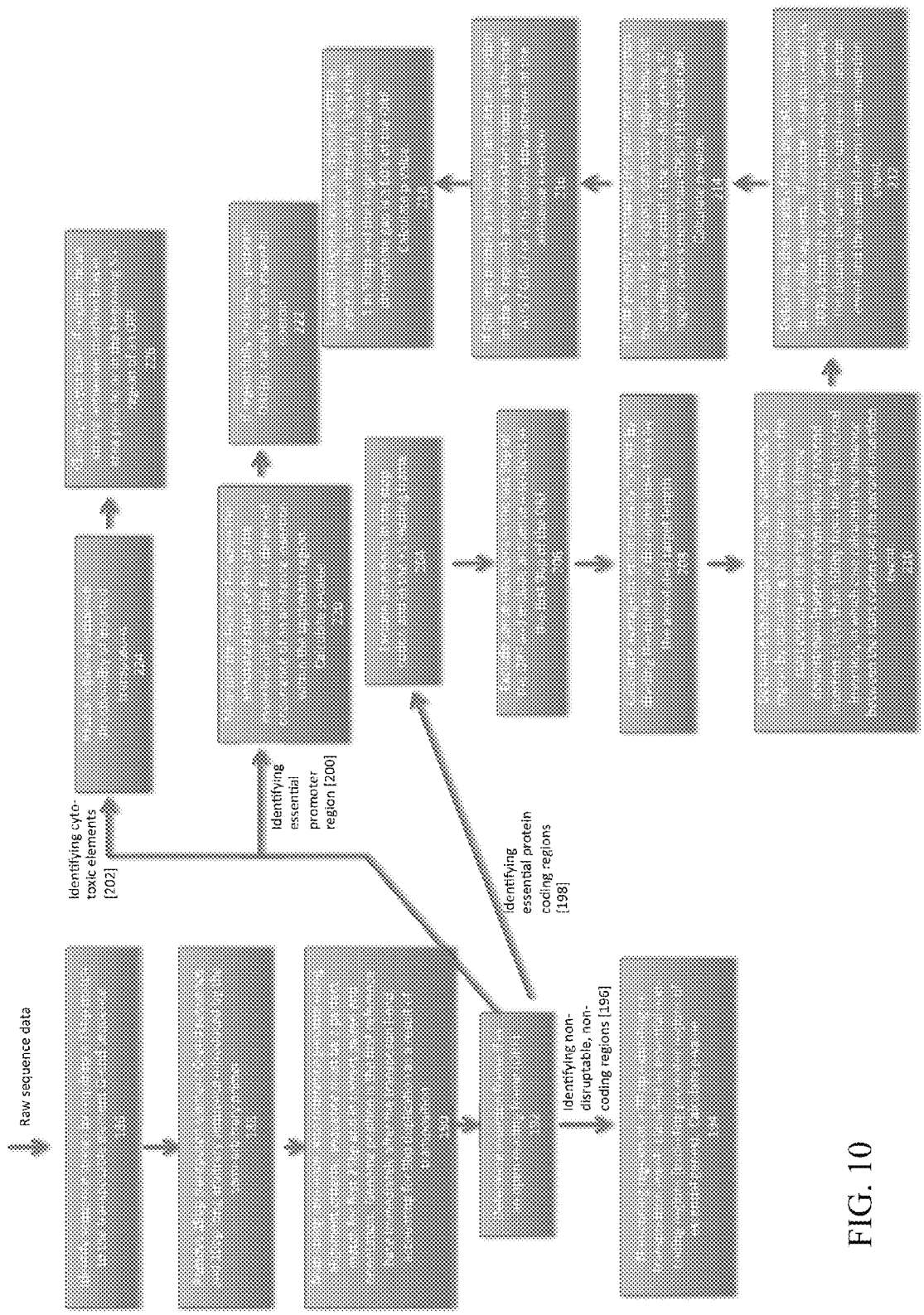
FIG. 10 is an exemplary flow chart outlining a computer-implemented method for mapping transposon insertion sites onto a reference genome and identifying essential genomic elements based on insertion frequency and bias.

In a preferred embodiment, the algorithm first identifies 186 sequencing string read outs by requiring a substantially perfect match to the last 15 bases of the O-end sequence 104 of the transposon element (GTGTATAAGAGTCAG) (SEQ ID NO: 1) (FIG. 10). This step separates out background noise and ensures that only sequences pertaining to transposon insertion events will be analyzed. The algorithm then further processes 188 the strings to remove the 19 bp long Tn5Pxyl O-end sequence 104 and the 10 bp long arbitrary sequence 140 of the semi-arbitrary primers, resulting in a sequence string of only native genomic sequence. The string is then mapped 190 onto a reference genome. In identifying 190 genome-wide transposon insertion site, the algorithm employs the following read alignment criteria: (1) a substantially perfect match onto the reference genome is required for the first 25 bp of each read and its mate, (2) each read and its mate have to be located in a correct paired-end orientation. The algorithm further accounts for the nine by long duplication that results from Tn5 transposition upon insertion into target DNA for insertion site analysis purposes by subtracting it out. The location of a given transposon insertion site is calculated 190 as the genome position of the first reference base detected immediately after reading out of the transposon I-end 108. The I-end 108 contains the outward point Pxyl promoter.

For every transposon insertion location within a coding region, the algorithm further determines 192 the insertion frame within the ORF. The Pxyl promoter 106 of the transposon element only permits transcription of downstream sequences for insertions located in the sense direction (frames +1, +2, +3). In addition, in this embodiment, the Tn5Pxyl element carries an engineered ribosome binding site 116 and an internal ATG codon immediately adjacent to the Pxyl promoter element. In this respect, insertions located in the +1 frame initiate translation at the internal ATG start codon and read through the I-end sequence 108 into the downstream coding sequence. As one of ordinary skill in the art would recognize, other embodiments of the algorithm and its selection and stringency criteria may be suitably modified for use with other transposon systems and genomes.

In a preferred embodiment, the algorithm identifies 196 non-disruptable non-coding genome elements by calculating the frequency of transposon insertions within designated non-coding sequences (FIG. 10). Non-coding DNA regions of at least 90 bp are considered 194 in the analysis and boundaries for non-disruptable elements are corrected by the algorithm to compensate for the 9 bp duplication generated upon Tn5 transposition. Further, within this analysis, the algorithm excludes 194 non-disruptable non-coding DNA regions located within the essential promoter region of essential genes.

In some embodiments, the algorithm performs 198 high-resolution mapping of all essential protein coding sequences 152 using an essential region heuristic. The algorithm calculates 208 the number of transposon insertions disrupting the coding region for every designated ORF while also excluding 204 insertions in the stop codon of an ORF or located in the +1 reading frame. Insertions targeting the stop codon of an ORF will not abrogate protein production while insertions located in the +1 frame will permit translation of downstream sequences due to the engineered RBS within the transposon element. The latter frame insertions do not necessarily abrogate protein function and could yield functional fusion proteins or split a given protein into two polypeptide fragments that retain the capability to assemble into a functional protein. The algorithm further omits 206 sense insertions in the last 9 bp of an ORF and anti-sense insertions targeting the first 9 bp since these insertions can still provide a full-length copy of the ORF due to the 9 bp duplication generated upon Tn5 transposition. The algorithm calculates 208 the average density of transposon insertions for every annotated ORF by dividing the number of disruptive transposon insertions by the target length of the ORF. This target length is defined as the length of the ORF in base pairs excluding the stop codon and subtracting 9 bp due to the duplication generated by Tn5 transposition. Additionally, the algorithm determines 210 for every ORF the length of the non-disrupted 5' region and calculates the distance between the start codon and the first not in-frame insertion event downstream. If a second insertion event is detected no further than 100 bp apart from the first internal insertion event, the algorithm designates the measurement as robust. Otherwise, the algorithm designates the first insertion event as noise and the length of the non-disrupted 5' region is calculated as the distance between the start codon and the second insertion event.

Furthermore, the algorithm calculates 212 for every coding region the length of the largest internal non-disruptable coding segment detected employing similar robustness criteria as that used for determining the non-disrupted 5' region. The essential region heuristic classifies 214 ORFs 214 as essential if the non-disruptable 5' region covers more than 60% of the total ORF length. In order to identify essential ORFs that might be mis-annotated, the essential region heuristic also classifies 218 ORFs as essential if the ORF shows an insertion density of less than one insertion in 50 bps and the largest non-disruptable internal gap identified covers more than 60% of the total ORF length. The heuristic further re-annotates 216 the start codons of essential ORFs if anti-sense insertions are detectable within 5' regions, choosing the closest ATG, GTG or TTG codon positioned downstream of an anti-sense insertion. ORFs that show an insertion density of less than one insertion every 25 bp and harbor a non-disruptable 5' region covering less than 60% of the total ORF length are classified by the algorithm as non-essential ORFs with high fitness costs.

In some embodiments, the algorithm identifies 202 cytotoxic genetic elements by first assessing 224 the sequence directionality (sense or antisense) of inserted transposon elements and them computing insertion bias (FIG. 10). The algorithm designates 226 areas that demonstrate strong bias towards antisense insertions in areas prior to or in the beginning 5' region of ORFs as potential cyto-toxic genetic elements. Sense insertions in these areas of an ORF will cause upregulation of these elements, and consequently, cause a lethal phenotype.

Figure 8A:
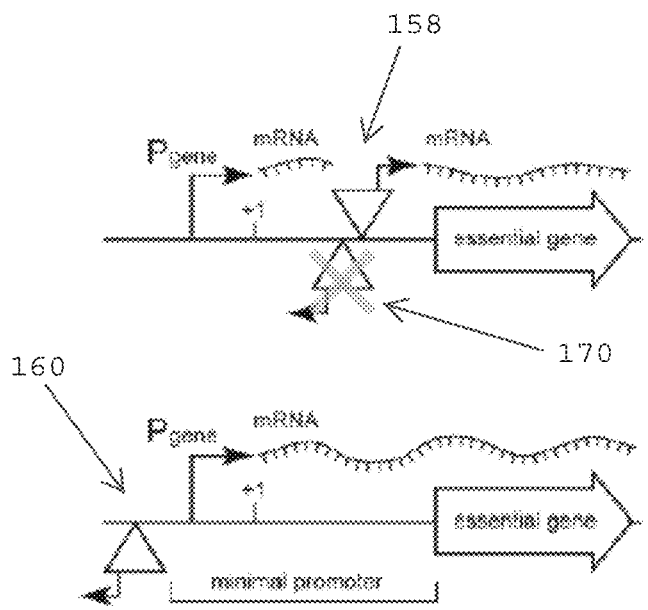
FIG. 8A illustrates an example of mapping the essential promoter of an essential gene which comprises measuring the distance between the annotated start codon of the ORF and the first anti-sense insertion upstream while FIG. 8B similarly illustrates an example of mapping an essential operon, which harbors essential promoter regions that fully include one or more upstream ORFs.
Figure 8B:
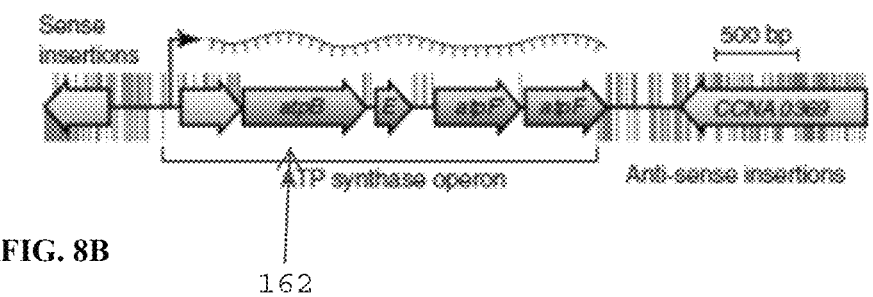

In some embodiments, the algorithm identifies 200 essential promoter elements for essential genes (FIGS. 8, 10). Specifically, transposon insertions within the promoter region of an essential gene are only viable if the transposon-specific promoter is oriented in the sense direction 158; insertions in the anti-sense direction are lethal 170 (FIG. 8A). To this extent, the algorithm measures 220 the distance between the annotated start codon of the ORF of an essential gene and the first detected occurrence of an anti-sense insertion within the upstream region 160 to identify an essential gene's essential promoter region. Similarly, the algorithm identifies the essential promoter regions of essential RNAs by measuring the distance between the annotated start of the RNA element and the first anti-sense insertion detected upstream. In some embodiments, the algorithm identifies 222 essential operons by determining if ORFs harboring essential promoter regions fully include one or more upstream ORFs 162 (FIG. 8B).

In some embodiments, the algorithm calculates p-values 172 for essentiality for each identified non-disruptable genome region (FIG. 10). P-values 172 are calculated according to $$p_{(l)} = \left(1 - \frac{l}{g_{size}}\right)^{n_{Tn5}}$$

where $p_{(l)}$ is the p-value to observe no transposon insertion events within a genome region of length l or longer, $g_{size}$ is the size of the target genome in base pairs; l is the length of the non-disruptable genome region in base pairs; $n_{Tn5}$ is the estimated number of independent Tn5 insertions present within the entire transposon mutant library. $n_{Tn5}$ is approximated according to:

$$n_{Tn5} = \frac{\log_{10}\left(1 - \frac{n_{mapped}}{2g_{size}}\right)}{\log_{10}\left(1 - \frac{1}{2g_{size}}\right)}$$

where $n_{mapped}$ is the number of unique Tn5 insertion sites mapped. The algorithm assumes uniform distribution of insertion sites within nonessential genomic regions and neutral fitness costs for every possible insertion generated at any genome location for calculation purposes.

The identification of the essential genomic elements of an organism will have many critical and significant medical and industrial applications. For instance, the selection of bacteria under conditions suited to particular hosts will allow for the identification of genes involved in pathogenicity and persistence in host organisms as these genes will be essential for viability. This in turn will enable a greater microbiological understanding of bacteria as well as reveal important targets for the development of novel antibiotic agents. Furthermore, dissecting the essential genome of a bacterium will allow for the identification of genes involved in antibiotic resistance itself, an increasingly alarming health problem in the world today. In this respect, performing hyper-saturated transposon mutagenesis on resistant bacteria and selecting it under the presence of the respective antibiotic would reveal the underlying genes critical for resistance by contrasting it with the essential genome of the respective non-resistant bacterium. Additionally, pathways involved in specific metabolic or catabolic reaction networks such as those useful for biofuel production or bioremediation applications could be identified by selecting for mutagenized bacteria in the relevant nutritional environment. For instance, genomic elements necessary for the generation of cellulosic ethanol could be deduced by selecting particular strains of an organism in a stringent cellulose-based environment. Similarly, genomic elements critical for oil degradation for use in oil spills could be isolated by selecting relevant strains in a petroleum-based environment. Moreover, the identification of cyto-toxic elements, which prove lethal to bacteria when overexpressed, will further provide a new arsenal of tools for anti-microbial drug development.

EXAMPLES

The following discloses embodiments that are merely representative of the technology, which may be embodied in various other forms. Thus, specific compositional and methodological details disclosed herein are not to be interpreted as limiting.

Essential Genome of *Caulobacter crescentus*
Construction of Transposon Delivery Plasmid A Tn5 transposase and an adjacent ampicillin resistance cassette was PCR amplified from a plasmid bearing these genes (pIT2) using primer #1 and primer #2:

```
Primer #1
                                       (SEQ ID: NO 2)
CATATGGGAGATCTGATCAAGAGACAGGTCGACCGATCCCGTACA
CAAGTAGC Primer #2
                                       (SEQ ID NO: 3)
AGAGCTCGCGTCACACTCATCGGTTGGGTGACACTCTTTCCCTAC
ACGACGCTCTTCCGATCTACTTGTGTATAAGAGTCAGTTACC
```

Primer #1 incorporated the Tn5 I-end sequence and a NdeI site. Primer #2 introduced the Tn5 O-end sequence, the Illumina paired-end adapter sequence (PE 1.0, Illumina, Hayward, Calif.) and a Sac I site. The PCR product was cloned into pCR2.1-TOPO® and further subcloned via NdeI, SacI into plasmid pXMCS2 to produce the transposon delivery plasmid pXMCS2::Tn5Pxyl. The Tn5Pxyl element harbors at one end an outward pointing Pxyl promoter. Depending on the orientation of a given Tn5Pxyl insertion, the outward facing Pxyl promoter will permit expression of adjacent genes.

The transposon delivery plasmid pXMCS2::Tn5Pxyl was conjugated from an E. Coli S17-1 donor strain into a *Caulobacter* ΔrecA strain. Transposition events were selected onto PYE plates containing kanamycin (20 µg/ml) and nalidixic acid (20 µg/ml) and 0.1% xylose. PYE plates were incubated at 30° C. for 7 days till kanamycin resistant colonies were deposited into individual wells of 96-well plates. The resulting Tn5Pxyl insertion library contained an estimated $8 \times 10^5$ transposon mutants.

DNA Library Preparation and DNA Sequencing

DNA fragments that cover transposon junctions from each mutant pool were simultaneously amplified by a semi-arbitrary PCR strategy. (FIG. 2A). PCR reactions were performed in 96 well format on a DNA Engine Tetrad Thermocycler (MT Research, Waltham, Mass.) using BioMix® Red (Bioline, Tauton, Mass.). For each transposon mutant pool 1 µl of a bacterial culture (OD 1.0) was directly added to individual PCR reactions as template. Terminal adapter sequences compatible to the Illumina sequencing process were amplified from the engineered linker adjacent to the Tn5Pxyl O-end as well as introduced via the PCR primers (#4, #5, #6).

```
Primer #4
                                          (SEQ ID NO: 4)
CTCGGCATTCCTGCTGAACCGCTCTTCCGATCTNNNNNNNNNNACGCC Primer #5
                                          (SEQ ID NO: 5)
CTCGGCATTCCTGCTGAACCGCTCTTCCGATCTNNNNNNNNNNCCTGG Primer #6
                                          (SEQ ID NO: 6)
CTCGGCATTCCTGCTGAACCGCTCTTCCGATCTNNNNNNNNNNCCTCG
```

Each semi-arbitrary primer contained a defined 3' pentanucleotide sequence, an interspacing 10 bp long arbitrary sequence, and a 5' PE2.0 adapter sequence (FIG. 2B). The three semi-arbitrary primers possess different 3' pentanucleotide sequences that each anneal on average every 300 bp throughout the Caulobacter genome. The first round of PCR was performed with the following program: (1) 94° C. for 3 min, (2) 94° C. for 30 s, (3) 42° C. for 30 s, slope −1° C. per cycle, (4) 72° C. for 1 min, (5) go to step 2, 6 times, (6) 94° C. for 30 s, (7) 58° C. for 30 s, (8) 72° C. for 1 min, (9) go to step 6, 25 times, (10) 72° C. for 3 min.

First-round PCR products were further amplified in a second nested PCR step using the Illumina paired-end primer PE1.0 and PE2.0 (#7, #8) and 2 µl of the first round PCR product as template.

```
Primer #7
                                          (SEQ ID NO: 7)
AATGATACGGCGACCACCGAGATCTACACTCTTTCCCTACACGA
CGCTCTTCCGATCT Primer #8
                                          (SEQ ID NO: 8)
CAAGCAGAAGACGGCATACGAGATCGGTCTCGGCATTCCTGCT
GAACCGCTCTTCCGATCT
```

Primer #7 anneals to the engineered Illumina paired-end sequence adjacent to the transposon O-end. Primer #8 anneals to the 5' tag sequence previously introduced by the first-round semi-arbitrary primers (#4, #5, #6). Second-round PCR was thermo-cycled using the following parameters: (1) 94° C. for 3 min, (2) 94° C. for 30 s, (3) 64° C. for 30 s, (4) 72° C. for 1 min, (5) go to step 2, 30 times, (6) 72° C. for 3 min. Second-round PCR products derived from an estimated 4–5×10$^5$ transposon mutants were pooled according to the semi-arbitrary primer used. DNA fragments of 140 bp-700 bp were size selected and purified by agarose gel electrophoresis prior to Illumina sequencing.

Illumina Sequencing and Processing

Cluster-generation was performed within standard Illumina paired-end flow-cells (Illumina cluster chemistry v2) and settings according to the Illumina cluster generation protocol. The DNA sample concentration of each transposon junction library was titrated to produce approximately 1.3× 10$^5$ clusters per tile on the flow cell. Paired-end sequencing with 76 bp read length from both ends of a given DNA fragment was performed on an Illumina GAIIx instrument. Sequencing chemistry v4 and standard paired-end sequencing primers (PE 1.0 and PE 2.0, Illumina) were used.

Base-calling from raw images was performed using the genome analyzer software suite OLB version 1.6 (Illumina). A phiX control lane was specified to calculate crosstalk matrixes and calibrate phasing parameters. Sequencing strings reading out of the Tn5Pxyl transposon elements were identified by requiring a perfect match to the last 15 bases of the O-end sequence (GTGTATAAGAGTCAG) (SEQ ID NO: 1). Paired-end reads were further processed to remove the 19 bp long Tn5Pxyl O-end sequence and the by long arbitrary sequence of the semi-arbitrary primers. The resulting reads contained Caulobacter specific DNA strings that were subsequently mapped onto the *Caulobacter crescentus* NA1000 reference chromosome. A SNPs and Indels analysis was performed to identify any sequencing error sites within the reference *Caulobacter crescentus* NA1000 genome. Sequencing error could lead to some small sites being incorrectly deemed essential. The SNP and Indel analysis showed that the genome sequence of the *Caulobacter*_recA strain used in this study was identical to the published reference genome sequence of *Caulobacter crescentus* NA1000 with the exception of the engineered 700 bp deletion covering part of the recA gene. The previously described algorithm and essential region heuristic was employed to map and analyze transposon insertion sites for the identification of non-disruptable non-coding genome elements, essential protein coding regions, and essential promoters and operons, the results of which are summarized in Table I.

Overall, a single sequencing run yielded 118 million raw sequencing reads. Of these, >90 million (>80%) read outwards from the transposon element into adjacent genomic DNA regions and were subsequently mapped to the 4-Mbp genome, allowing us to determine the location and orientation of 428,735 independent transposon insertions with base-pair accuracy (FIG. 4). Eighty percent of the genome sequence showed an ultrahigh density of transposon hits; an average of one insertion event every 7.65 bp. The largest gap detectable between consecutive insertions was <50 bp. Within the remaining 20% of the genome, chromosomal regions of up to 6 kb in length tolerated no transposon insertions.

TABLE I

The essential Caulobacter genome

|  | Quantity | Size (bp) | Fraction of genome (%)$^a$ |
|---|---|---|---|
| Essential non-coding elements | 130 | 14 991 | 0.37 |
| Non-coding elements, unknown function | 91 | 10 893 | 0.27 |
| tRNAs | 29 | 2312 | 0.06 |
| Small non-coding RNAs | 8 | 1488 | 0.04 |
| Genome replication elements in the Cori | 2 | 298 | 0.01 |
| Essential ORFs | 480 | 444 417 | 11.00 |
| Metabolism | 176 | 160 011 | 3.96 |
| Ribosome function | 95 | 76 420 | 1.89 |
| Cell wall & membrane biogenesis | 54 | 63 393 | 1.57 |
| Proteins of unknown function | 49 | 30 469 | 0.75 |
| Cell cycle, division and DNA replication | 43 | 52 322 | 1.29 |
| Other cellular processes | 39 | 36 017 | 0.89 |
| Transcription | 15 | 16 417 | 0.41 |
| Signal transduction | 9 | 9368 | 0.23 |
| Essential promoter regions | 402 | 33 533 | 0.83 |

TABLE I-continued

The essential Caulobacter genome

| | Quantity | Size (bp) | Fraction of genome (%)$^a$ |
|---|---|---|---|
| Contained within intergenic sequences | 210 | 13 150 | 0.33 |
| Extending into upstream ORFs | 101 | 11 428 | 0.28 |
| Driving operons | 91 | 8955 | 0.22 |
| Essential Caulobacter genome | | 492 941 | 12.19 |

Identification of Non-Disruptable Non-Coding Genome Elements

Within non-coding sequences of the Caulobacter genome, we detected 130 small non-disruptable DNA segments between 90 and 393 bp long. Among 27 previously identified and validated sRNAs (Landt et al., 2008), three (annotated as R0014, R0018 and R0074 in Landt et al., 2008) were contained within non-disruptable segments while another three (R0005, R0019 and R0025) were partially disruptable (FIG. 6A). Two additional small RNAs found to be essential are the transfer-messenger RNA (tmRNA) and the ribozyme RNAseP (Landt et al., 2008). In addition to the 8 non-disruptable sRNAs, 29 out of the 130 essential non-coding sequences contained non-redundant tRNA genes; duplicated tRNA genes were found to be non-essential. We identified two non-disruptable DNA segments within the chromosomal origin of replication. A 173-bp long essential region contains three binding sites for the replication repressor CtrA, as well as additional sequences that are essential for chromosome replication and initiation control (Marczynski et al., 1995). A second 125 bp long essential DNA segment contains a binding motif for the replication initiator protein DnaA.

High-resolution Mapping of all Essential Protein Coding Sequences

We identified 480 essential ORFS and 3240 non-essential ORFS among the 3876 annotated ORFs of Caulobacter (see e.g. FIG. 5). In all, 145/480 essential ORFs lacked transposon insertions across the entire coding region, suggesting that the full length of the encoded protein up to the last amino acid is essential. The 7.65-bp resolution allow a dissection of the essential and non-essential regions of the coding sequences. Sixty ORFs had transposon insertions within a significant portion of their 3' region but lacked insertions in the essential 5' coding region, allowing the identification of non-essential protein segments. For example, transposon insertions in the essential cell-cycle regulatory gene divL, a tyrosine kinase, showed that the last 204 C-terminal amino acids did no impact viability, confirming previous reports that the C-terminal ATPase domain of DivL is dispensable for viability (FIG. 6B). Our results show that the entire C-terminal ATPase domain, as well as the majority of the adjacent kinase domain, is non-essential while the N-terminal region including the first 25 amino acids of the kinase domain contain essential DivL functions (FIG. 6B).

Conversely, we found 30 essential ORFs that tolerated disruptive transposon insertions within the 5' region while no insertion events were tolerated further downstream. One such example, the essential histidine phosphotransferase gene chpT, had 12 transposon insertions near the beginning of the annotated ORF. These transposon insertions would prevent the production of a functional protein and should not be detectable within chpT or any essential ORF unless the translational start site is mis-annotated. Cumulatively, >6% of all essential ORFs (30 out of 480) appear to be shorter than the annotated ORF, suggested that these are probably mis-annotated, as well. The remaining 245 ORFs tolerated occasional insertions within a few amino acids of the ORF boundaries.

The majority of the essential ORFs have annotated functions. They participate in diverse core cellular processes such as ribosome biogenesis, energy conversion, metabolism, cell division and cell-cycle control. Forty-nine of the essential proteins are of unknown function. Among the 480 essential ORFs, there were 10 essential transcriptional regulatory proteins, including the cell-cycle regulators ctrA, gcrA, ccrM, sciP, dnaA, plus 5 uncharacterized putative transcription factors. In addition, two RNA polymerase sigma factors RpoH and RpoD, as well as the anti-sigma factor ChrR, which mitigates rpoE-dependent stress response under physiological growth conditions, were also found to be essential.

Essential Promoter and Operon Analysis

We found the promoter regions of 210 essential genes to be fully contained within their respective upstream intergenic sequences. The promoter regions of 101 essential genes extended upstream into flanking ORFs. We also identified 206 essential genes that are co-transcribed with their corresponding flanking gene(s) and we experimentally mapped 91 essential operon transcripts. Altogether, we found that the 480 essential protein-coding and 37 essential RNA-coding Caulobacter genes are organized into operons such that 402 individual promoter regions are sufficient to regulate their expression.

The invention claimed is:

1. A method for determining genetic elements of an organism's genome, the method comprising:
performing hyper-saturated transposon mutagenesis to generate an engineered transposon comprising a Tn5 O-end insertion primer having the sequence of SEQ ID NO: 3, and a Tn5 I-end primer having the sequence of SEQ ID NO. 2;
said hyper-saturated transposon mutagenesis having a transposition density from about 8 to 100 bp;
selecting for viable mutants in the engineered transposon under a given selection condition;
pooling the selected viable mutants;
isolating transposon junctions through a shared parallel PCR strategy utilizing a first primer that is transposon specific, at least one semi-arbitrary primer, and at least one adaptor sequence primer, wherein the at least one semi-arbitrary primer is selected from the group consisting of SEQ ID NO. 4, SEQ ID NO. 5, and SEQ ID NO. 6;
sequencing the isolated transposon junctions in the ultra high-throughput adaptor based DNA sequencer;
mapping transposon insertion sites onto the organism's genome; and identifying the genetic elements based on frequency, locations and insertion orientation of the mapped transposon insertion sites.

2. The method of claim 1, wherein the engineered transposon further comprises an inducible outward pointing promoter.

3. The method of claim 1, wherein the engineered transposon further comprises a first ribosomal binding site and a start codon located between an outward pointing promoter and a transposon end.

4. The method of claim 3, wherein the engineered transposon further comprises a second ribosomal binding site preceding the start codon.

5. The method of claim 1, wherein the engineered transposon is compatible with a Tn5 transposase.

6. The method of claim 2, wherein the outward pointing promoter is a Pxyl promoter.

7. The method of claim 1, wherein said parallel PCR comprises a nested PCR approach.

8. The method of claim 1, wherein the at least one adaptor sequence primer anneals to a first adaptor sequence of the engineered transposon to provide 5' to 3' amplification; and the at least one semi-arbitrary primer comprises a defined 3' penta- nucleotide sequence, an interspacing 10 bp long arbitrary sequence, and the 5' second adaptor sequence to provide 5' to 3' amplification.

9. The method of claim 8, wherein the at least one semi-arbitrary primers anneal on average from every 1000 bp to 300 bp throughout the organism's genome.

10. The method of claim 8, wherein the at least one semi-arbitrary primer employed following a first round of PCR amplification comprises a first semi-arbitrary primer which anneals to the first adaptor sequence and a second semi-arbitrary primer which anneals to the 5' second adaptor sequence.

11. The method of claim 1, wherein an algorithm maps transposon insertion sites onto the organism's genome and identifies genetic elements based on genomic transposition frequency.

12. The method of claim 11, wherein the algorithm identifies non-disruptable noncoding genome elements of at least 90 bp in length.

13. The method of claim 11, wherein the algorithm detects promoter regions of open reading frames (ORFs) by measuring the distance between an annotated start codon of the ORF and a first anti-sense upstream insertion.

14. The method of claim 13, wherein the algorithm classifies ORFs harboring an essential promoter region fully including one or more upstream ORFs as essential operons.

15. The method of claim 11, wherein the algorithm detects essential promoter regions of essential RNA elements by measuring a distance between an annotated transcriptional start of an RNA element and a first anti-sense upstream insertion.

16. The method of claim 11, wherein the algorithm calculates p-values for essentiality.

17. The method of claim 11, wherein the algorithm identifies cytotoxic genetic elements by identifying genomic regions with an insertional bias in an antisense orientation.

18. The method of claim 1, wherein the at least one adaptor sequence primer is selected from the group consisting of SEQ ID NO. 7 and SEQ ID NO. 8.

* * * * *

UNITED STATES PATENT AND TRADEMARK OFFICE
CERTIFICATE OF CORRECTION

| | |
|---|---|
| PATENT NO. | : 9,150,916 B2 |
| APPLICATION NO. | : 13/532674 |
| DATED | : October 6, 2015 |
| INVENTOR(S) | : Beat Christen et al. |

Page 1 of 1

It is certified that error appears in the above-identified patent and that said Letters Patent is hereby corrected as shown below:

In the specification:

Column 1, Line 12, please insert the following section:

-- Government License Rights
This invention was made with Government support under contract DE-FG02-05ER64136 awarded by the Department of Energy and under contracts GM051426, GM070972, and GM073011 awarded by the National Institutes of Health. The Government has certain rights in this invention. --

Signed and Sealed this
Eighth Day of March, 2016

Michelle K. Lee
*Director of the United States Patent and Trademark Office*